US00PP27191P3

(12) United States Plant Patent
Moon

(10) Patent No.: US PP27,191 P3
(45) Date of Patent: Sep. 27, 2016

(54) LAUREL OAK TREE NAMED 'QHMTF'

(50) Latin Name: *Quercus hemisphaerica*
Varietal Denomination: QHMTF

(71) Applicant: Southern Selections, LLC, Loganville, GA (US)

(72) Inventor: Dwayne C. Moon, Loganville, GA (US)

(73) Assignee: Southern Selections, LLC, Loganville, GA (US)

( * ) Notice: Subject to any disclaimer, the term of this patent is extended or adjusted under 35 U.S.C. 154(b) by 246 days.

(21) Appl. No.: 13/999,127

(22) Filed: Jan. 16, 2014

(65) Prior Publication Data

US 2015/0201539 P1 Jul. 16, 2015

(51) Int. Cl.
*A01H 5/00* (2006.01)

(52) U.S. Cl.
USPC ..... Plt./225

(58) Field of Classification Search
USPC ..... Plt./225, 216
See application file for complete search history.

(56) References Cited

U.S. PATENT DOCUMENTS 5,461,824 A 10/1995 Cassell

OTHER PUBLICATIONS

Dirr, M. 1998. 'Manual of Woody Landscape Plants'. Stipes Publishing, LLC, Champaign, Illinois.*

* cited by examiner

*Primary Examiner* — Susan McCormick Ewoldt
*Assistant Examiner* — Karen Redden
(74) *Attorney, Agent, or Firm* — Stinson Leonard Street LLP

(57) ABSTRACT

A Laurel oak tree (*Quercus hemisphaerica*) named "QHMTF" having a compact habit with dense canopy, vigorous growth rate, shiny rich dark green foliage in summer, and semi-evergreen holding leaves until late spring and also capable of being reproduced reliably from vegetative cuttings.

6 Drawing Sheets

Latin name: *Quercus hemisphaerica.*
Varietal denomination: 'QHMTF'.

BACKGROUND OF THE INVENTION

The present invention relates to a new and distinct variety of Laurel Oak Tree (*Quercus hemisphaerica*), which I have named "QHMTF".

Discovery: I discovered my new tree in November of 2005 growing as a seedling in a production field in Loganville, Walton County, Ga., among a group of cultivated Laurel Oaks. These trees were grown from bare-root seedlings purchased of unknown *Quercus hemisphaerica* parents purchased in the winter of 2000 from a nursery in Florida. In the winter of 2003, these liners were relocated from my liner field to a production field. It was here that I discovered 'QHMTF'. Evaluation of this tree continues in this field in Walton County, Loganville, Ga.

Propagation: 'QHMTF' was asexually propagation by the method of vegetative cuttings at my direction in the summer of 2008 in Walton County, Ga. This propagation from softwood cuttings and resulting progeny has proven the characteristics of my new variety to be genetically stable. Furthermore, these observations have confirmed that my new variety represents a new and improved variety of Laurel Oak as particularly evidenced by the compact habit with dense canopy, dominant central leader, fibrous root system, vigorous growth rate, and shiny, rich, dark green foliage in summer and holding onto leaves until spring along with the fact that it is the only known *Quercus hemisphaerica* to be reproduced from softwood cuttings. These genetic traits can be consistently reproduced by asexual propagation.

Uniqueness: 'QHMTF' was discovered in a block of seedling Laurel Oak (unknown *Quercus hemisphaerica* parents) purchased from a supplier of liners in Florida. I claim that the genetic characteristics of this tree are the result of naturally occurring cross-pollination. Due to the nature of the seedling purchase, comparison of surrounding cross pollinators is not possible. The characteristics of my new tree along with the fact that it is the only known Quercus hemisphaerica to be reproduced from softwood cuttings distinguish it from other typical seedling Laurel Oak including 'Darlington'. At the time this tree was selected, I observed 'QHMTF' Laurel Oak as a 2" caliper tree exhibiting a compact, dense canopy, dominant central leader, and shiny, dark green foliage. The remainder of the trees in this block had irregular structure and medium green foliage color.

Use: 'QHMTF' was observed for a period of several years and is believed to be particularly useful for street tree planting and in large areas such as golf courses, commercial sites and parks. 'QHMTF' will also benefit growers who will profit from a fast growing tree with consistent form.

BRIEF SUMMARY OF THE INVENTION

Background: Laurel Oak is native to coastal plain and piedmont areas from southern New Jersey to Florida to east Texas and Southeast Arkansas. It thrives in the heat and humidity of the Southeast and can be found in established dune areas, scrub oak sandhills, stream banks and occasionally in mixed woods. Laurel Oak prefers moist, well-drained soils in these areas but adapt readily to harsh conditions. This species is typically pyramidal-rounded with ultimate height of 40 to 60 feet and spread of 30 to 40 feet. My new cultivar differs from the species in that it is asexually reproduced, has a compact habit with dense canopy, dominant central leader, fibrous root system, vigorous growth rate, and shiny, rich, dark green foliage in summer and holding onto leaves until spring. The ultimate height and width of 'QHMTF' is not known. I expect my new variety of Laurel Oak to perform as well as the species.

Industry Representation: Cultivated Laurel Oak is predominately represented in the industry by seedling material reproduced by acorn. This accounts for a high degree of variability in the industry, both in the landscape industry and nursery. Seedling Laurel Oak (including 'Darlington') is variable in growth rate and habit, typically does not have a central leader, has a sparse, shallow root system, and tends to be open in youth. At time of submission, I am not aware of any other commercially available cultivar Laurel Oak. 'QHMTF' has a compact habit with dense canopy, dominant central leader, fibrous root system, vigorous growth rate, shiny, rich, dark green foliage in summer and holding onto leaves until spring along; it is the only known *Quercus hemisphaerica* reproduced from softwood cuttings. These genetic traits can be consistently reproduced by asexual propagation which makes my selection uniquely different from seedling Laurel Oak (including 'Darlington') at time of submittal.

BRIEF DESCRIPTION OF THE DRAWINGS

The accompanying photographs depict the color of the tree and foliage of my new variety as nearly as is reasonably possibly to make the same in a color illustration of this character.

DETAILED DESCRIPTION OF THE INVENTION

Figure 1:
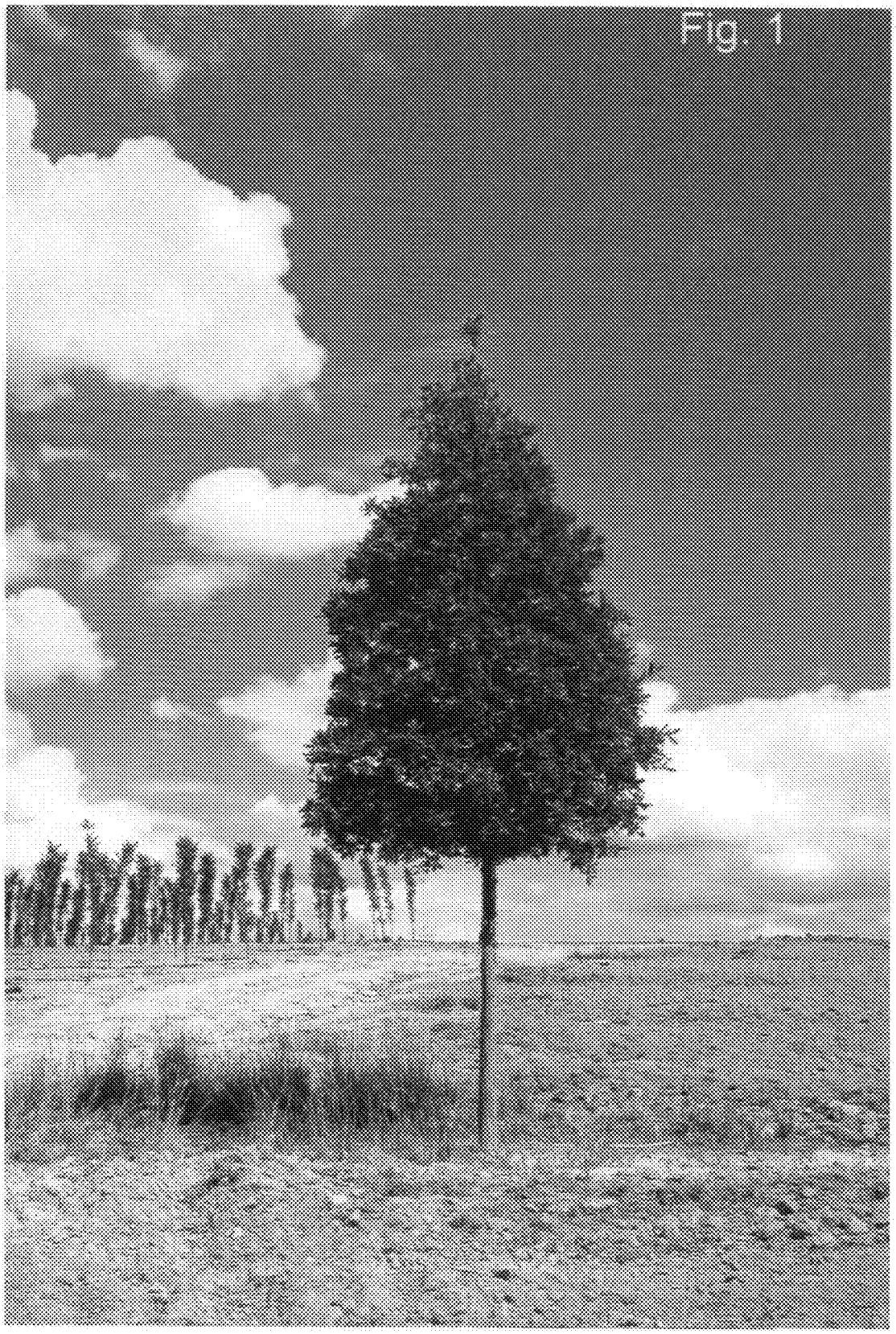
FIG. 1 is a photograph of the original parent 'QHMTF' variety from which the progeny are derived taken in the summer at seven years of age and four inch caliper at an observation area showing form and habit.
Figure 2:
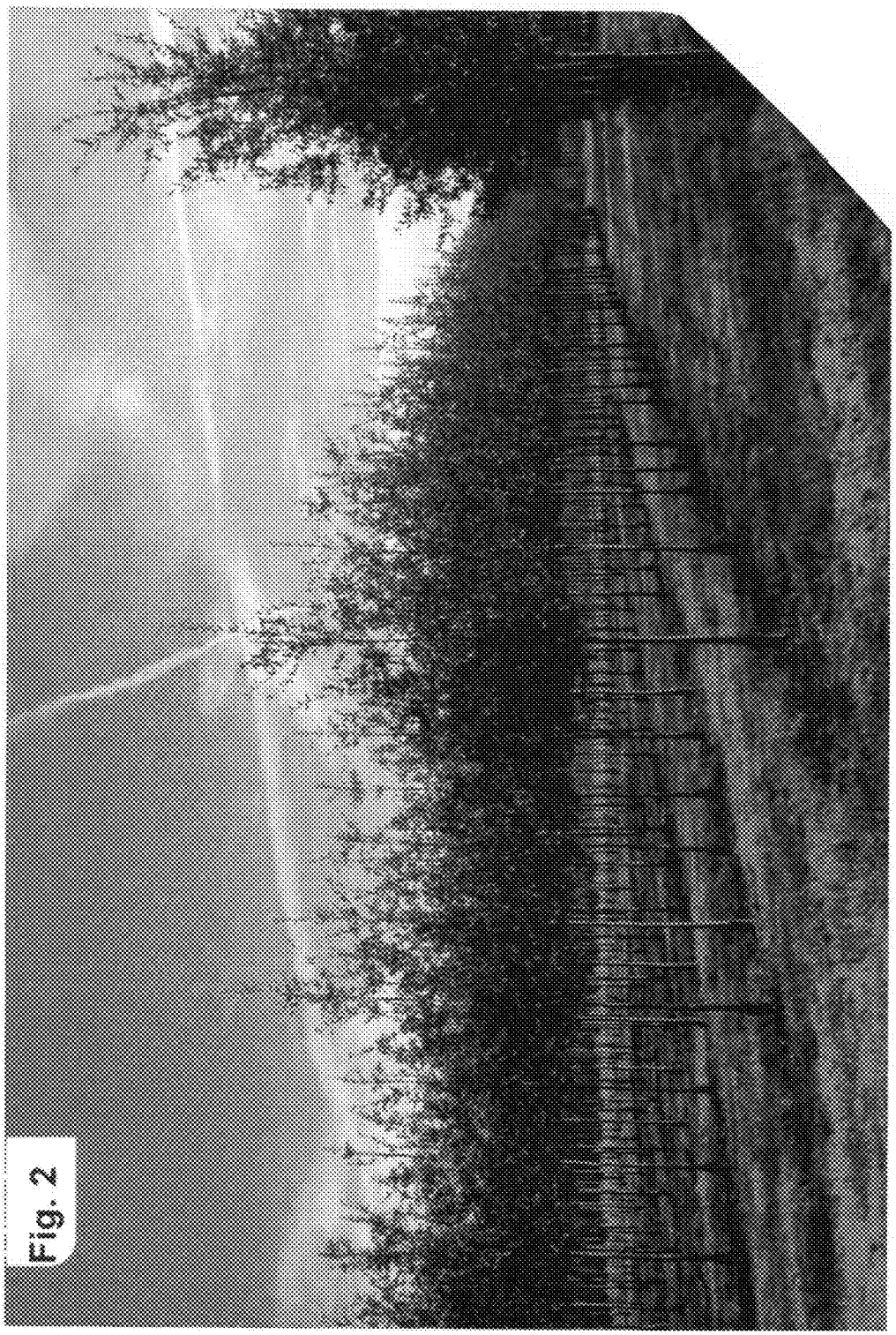
FIG. 2 is a field row photograph of the progeny in the fall at four years of age with each tree showing a dominant central leader and variations in fall color.
Figure 3:
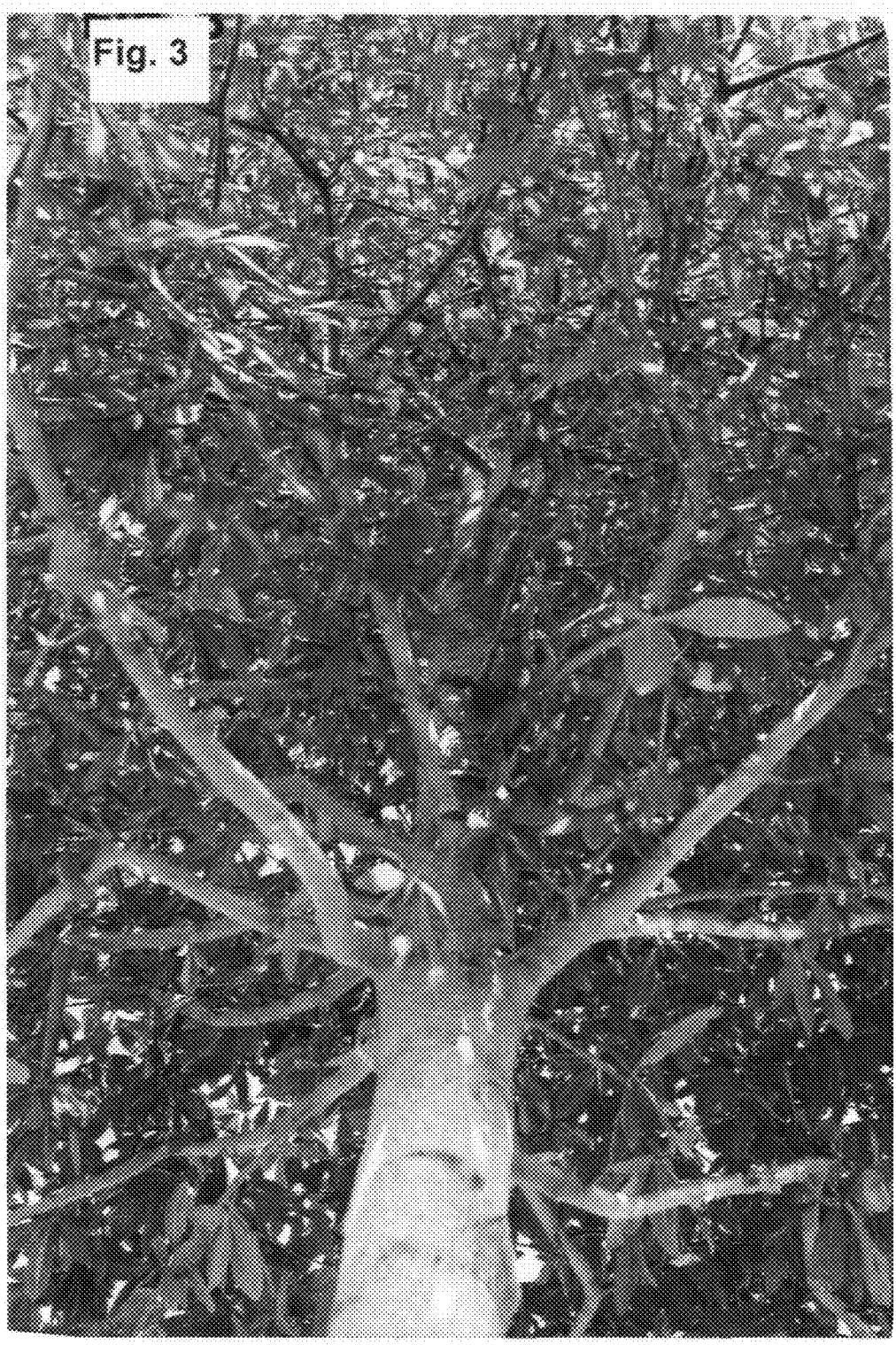
FIG. 3 is a photograph of the interior canopy of the progeny at four years of age showing a dominant central leader.
Figure 4:
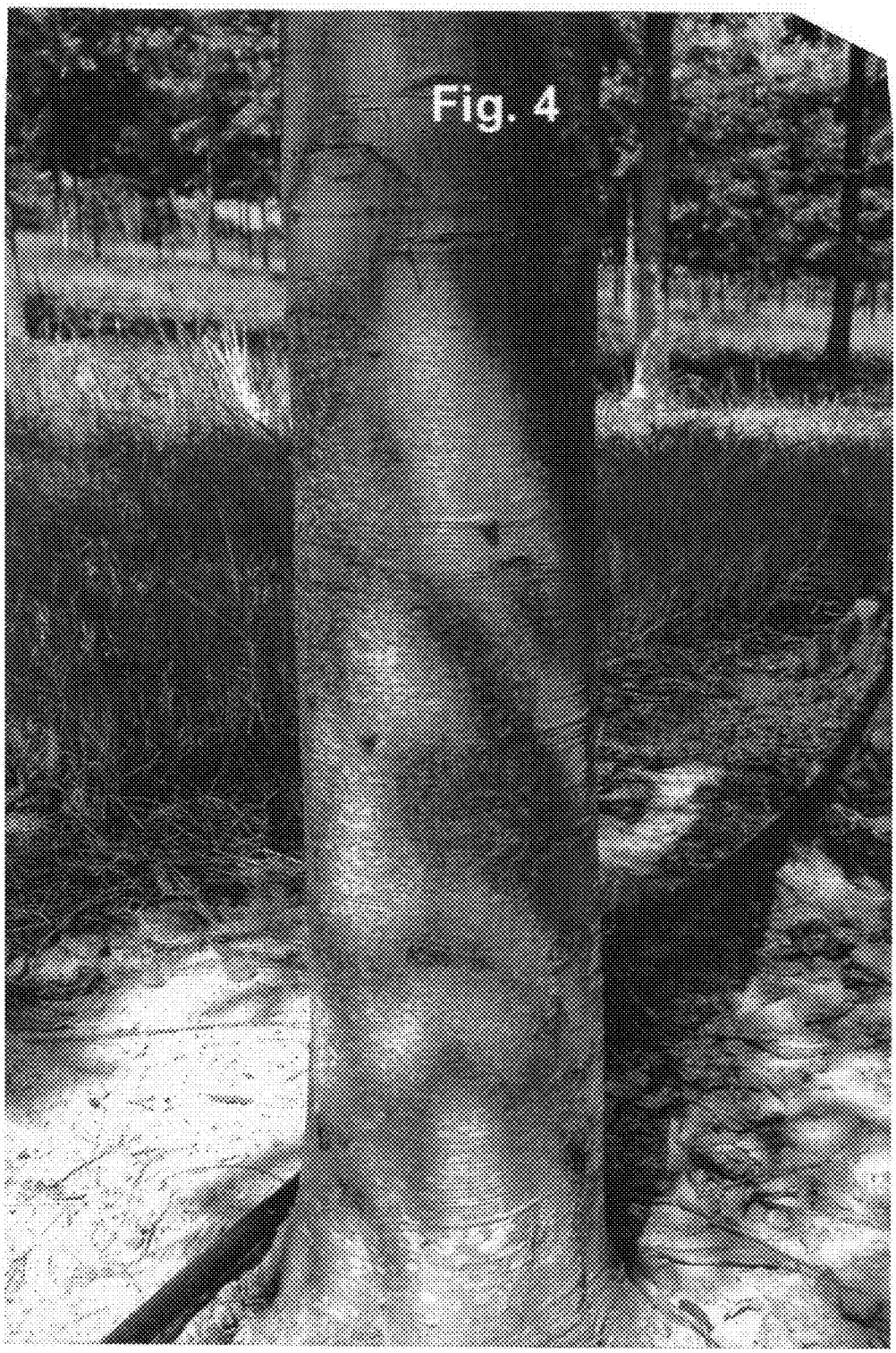
FIG. 4 is a photograph of the bark of the progeny taken at five inch caliper and seven years of age showing color and smoothness of my new variety.
Figure 5:
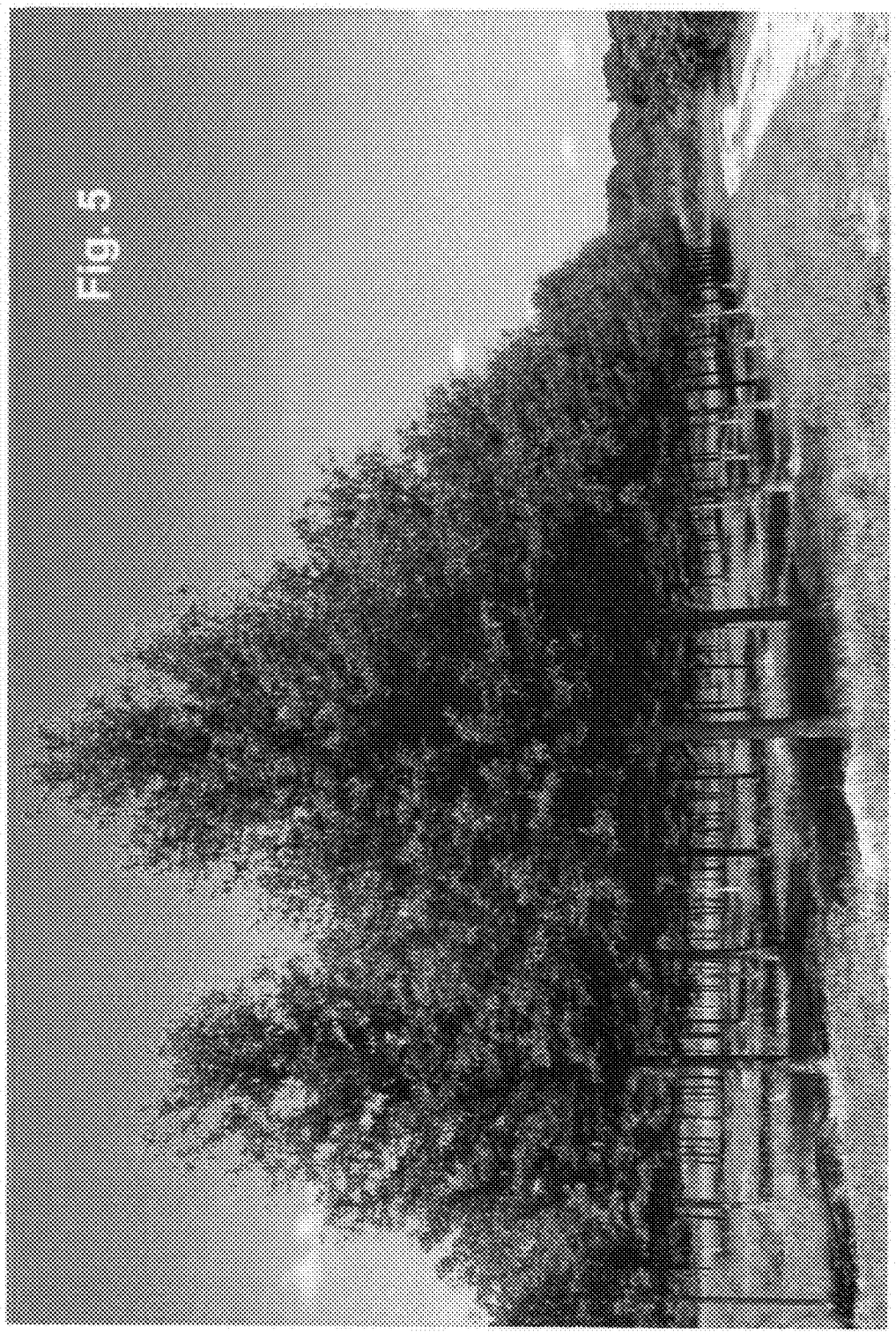
FIG. 5 is a field row shot of progeny taken at 5 inch caliper and seven years of age with each tree showing a dominant central leader.
Figure 6:
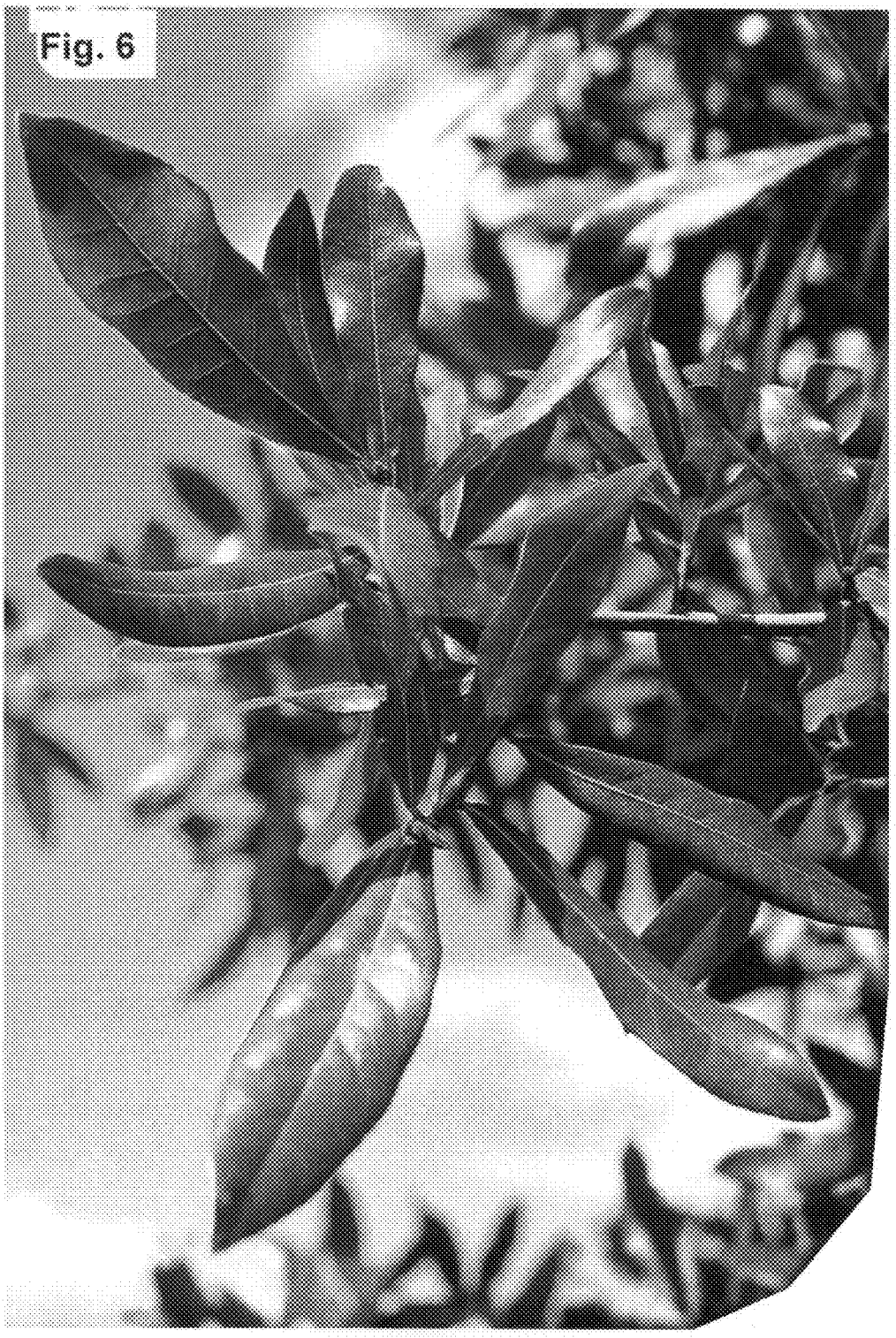
FIG. 6 is a photograph of the shiny, dark green foliage of the progeny at seven years of age.

Botanical Description of the Plant: The following is a detailed description of 'QHMTF' Laurel Oak with color terminology in accordance with The Royal Horticulture Society (R.H.S.) Colour Chart (2001) except where the context indicates a term having its ordinary dictionary meaning. My new tree has not been observed under all growing conditions, and variations may occur as a result of different growing conditions. All progeny of my new variety, insofar as have been observed, have remained genetically stable in all characteristics described hereinafter. Other than as set out hereinafter, as of this time, no other characteristics have been observed which are different from common Laurel Oak trees, which have been observed by the inventor.

Parentage: Naturally occurring cross-pollinated seedling of (unknown *Quercus hemisphaerica* parents) grown from bare-root liner purchased in the winter of 2001 from a nursery in Florida.

Locality where grown and observed: 'QHMTF' Laurel Oak trees are currently in production at in Walton County, Ga. This area of Walton County has a clay loam soil type with rainfall that varies between 30" and 60" annually. This particular area is located in USDA Hardiness Zone 7.

Size and growth rate: The original parent 'QHMTF' tree, aged 5 years measured 6.25" caliper at 12" above the ground. The height of 24' and spread of 13' provides a 1.85 height to width ratio. Average growth rate is between 1.00" to 1.25" per year.

Foliage: Typical of the species, alternate, simple, evergreen until spring, lanceolate, elliptic to oblanceolate, obovate, or oblong-obovate, 1.25" to 4" long, ½" to 1.25" wide, acute or obtuse, usually with a bristle-tip, cuneate or obtuse at base. The spring color emerges from a greyed-orange (RHS N170) to a yellow-green (RHS 144). Mature foliage is lustrous dark green above like (RHS 137A) and lighter green below like (RHS 137C). The fall color is a russet red like (RHS N167B). The petiole is 0.25" long, yellowish like (RHS 10B). The petiole diameter is 1/16".

Buds: Imbricate, shiny greyed purple like (RHS 183D) ⅛" to ¼" long, essentially glabrous, small for oak buds.

Flowers: Typical of species. Flowers are borne in clustered catkins in March and April, usually lasting for 10 to 14 days.

Fruit: Typical of the species being short-stalked (virtually sessile), the nut subglobose to ovoid about ½" in both diameter and length and brown in color like (RHS 200B) and enclosed ¼" by the saucer-shaped cap which is grey-brown like (RHS 199B).

Trunk: Typical of the species. The bark is initially smooth, and brown like (RHS N200B), becoming darker with maturity.

Branching: Slightly ascending to nearly horizontal at the base, emerging at 80-90 degrees from the trunk. Upper branches are more ascending, emerging at 45 degrees or more from the trunk. Color is brown like (RHS 200B).

Shape: Compact, pyramidal with dense branching and dominant central leader.

Root system: Fibrous, typical of *Quercus hemisphaerica.*

Vigor: The initially discovered tree has averaged between 1.0" to 1.25" in caliper per year. The root development from time of softwood cuttings to a finished rooted 3½" pot is five to seven weeks.

Disease: Free from disease.

Pests: Displays spider mite resistance but does show signs of mild leaf hopper damage.

What is claimed is:

1. A new and distinct variety of Laurel oak tree named "QHMTF" substantially as herein shown, illustrated and described, characterized particularly as to novelty by its compact habit with dense canopy, vigorous growth rate, shiny rich dark green foliage in summer, and semi-evergreen holding leaves until spring.

* * * * *